United States Patent
Samrano

(10) Patent No.: US 10,383,701 B2
(45) Date of Patent: Aug. 20, 2019

(54) GUIDING ASSEMBLY FOR DENTAL RESTORATION PROCEDURES

(71) Applicant: D-SHAPE NON-INVASIVE PRECISION DENTISTRY LTD, Allone Aba (IL)

(72) Inventor: Sergio Samrano, Allone Aba (IL)

(73) Assignee: D-SHAPE NON-INVASIVE PRECISION DENTISTRY LTD, Allone Aba (IL)

( * ) Notice: Subject to any disclaimer, the term of this patent is extended or adjusted under 35 U.S.C. 154(b) by 0 days.

(21) Appl. No.: 15/557,109

(22) PCT Filed: Mar. 9, 2016

(86) PCT No.: PCT/IL2016/050260
§ 371 (c)(1),
(2) Date: Sep. 10, 2017

(87) PCT Pub. No.: WO2016/142943
PCT Pub. Date: Sep. 15, 2016

(65) Prior Publication Data
US 2018/0042696 A1 Feb. 15, 2018

(30) Foreign Application Priority Data

Mar. 9, 2015 (IL) .......................... 237637
Nov. 5, 2015 (IL) .......................... 242477

(51) Int. Cl.
*A61C 1/08* (2006.01)
*A61C 3/02* (2006.01)
(Continued)

(52) U.S. Cl.
CPC ................ *A61C 1/082* (2013.01); *A61C 3/02* (2013.01); *A61C 9/0053* (2013.01); *A61C 13/0004* (2013.01); *A61C 13/0019* (2013.01)

(58) Field of Classification Search
CPC ........... A61C 1/082; A61C 1/088; A61C 3/02; A61C 9/0053; A61C 13/0004; A61C 13/0019
(Continued)

(56) References Cited

U.S. PATENT DOCUMENTS 472,004 A * 3/1892 Sweet et al. ........... A61C 1/084
433/75
1,407,840 A * 2/1922 Cruttenden .......... A61C 19/055
433/76
(Continued)

FOREIGN PATENT DOCUMENTS

WO WO-2009000505 A1 * 12/2008 ............. A61C 1/082
WO 2014113761 A1 7/2014

OTHER PUBLICATIONS

International Search Report of PCT/IL2016/050260, Completed Jun. 16, 2016; dated Jun. 21, 2016, 5 Pages.
(Continued)

*Primary Examiner* — Wade Miles
*Assistant Examiner* — Matthew P Saunders
(74) *Attorney, Agent, or Firm* — The Roy Gross Law Firm, LLC; Roy Gross

(57) ABSTRACT

A dental guidance assembly that includes: (a) a rigid body comprising at least one tooth-shaped recess and a coupling structure; and (b) at least two dental bur guides that are each: structured to securely and removably couple to said coupling structure, and comprising an elongated slot having the following measurements: a length of 4 to 40 millimeters, a width of 1 to 4 millimeters, and a depth of 2 to 10 millimeters. The elongated slot extends along a portion of a circumference of a treated tooth, wherein the elongated slots of said at least two dental bur guides have complementary structures, such that, together, the elongated slots are configured to facilitate a limitation of the motion of a dental bur
(Continued)

to: an entirety of the circumference of a treated tooth, and a depth suitable to form a shoulder on the treated tooth, for receiving a dental restoration.

8 Claims, 6 Drawing Sheets

(51) Int. Cl.
*A61C 9/00* (2006.01)
*A61C 13/00* (2006.01)

(58) Field of Classification Search
USPC .................................. 433/29, 72–76; 700/98
See application file for complete search history.

(56) References Cited

U.S. PATENT DOCUMENTS

| | | | | |
|---|---|---|---|---|
| 2,828,544 A * | 4/1958 | Ashkin | ................. | A61C 1/082 433/130 |
| 3,445,935 A * | 5/1969 | Marshall | ................. | A61C 1/082 433/51 |
| 3,600,810 A * | 8/1971 | Marshall | ................. | A61C 3/02 433/75 |
| 4,144,645 A * | 3/1979 | Marshall | ................. | A61C 5/77 433/223 |
| 7,004,757 B2 * | 2/2006 | Wilkinson | ............. | A61C 1/082 433/165 |
| 2003/0008262 A1 * | 1/2003 | Neuschafer | ............ | A61C 1/082 433/76 |
| 2004/0043355 A1 * | 3/2004 | Jonsson | ................. | A61C 1/082 433/75 |
| 2010/0192375 A1 * | 8/2010 | Jacquemyns | ............ | A61C 3/02 29/896.1 |
| 2012/0143364 A1 * | 6/2012 | McLeod | ................. | A61C 1/082 700/98 |
| 2013/0337412 A1 * | 12/2013 | Kwon | .................... | A61C 1/082 433/183 |
| 2014/0205968 A1 * | 7/2014 | Jung | ...................... | A61C 1/082 433/75 |
| 2014/0242541 A1 * | 8/2014 | Jung | ...................... | A61C 1/082 433/74 |
| 2014/0248577 A1 * | 9/2014 | Tahmasebi | ............. | A61C 1/082 433/75 |
| 2014/0316750 A1 * | 10/2014 | Jung | ...................... | A61C 1/082 703/1 |
| 2016/0143717 A1 * | 5/2016 | Samrano | ................ | A61C 1/082 29/896.1 |

OTHER PUBLICATIONS

Written Opinion of PCT/IL2016/050260, Completed Jun. 19, 2016; dated Jun. 21, 2016, 3 Pages.

* cited by examiner

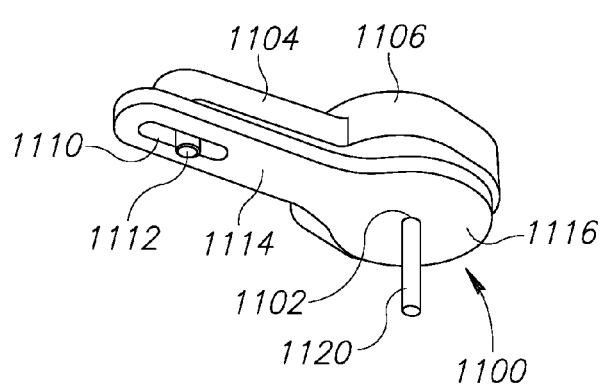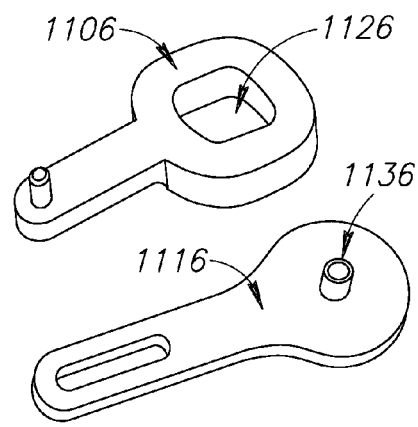
FIG.11A  FIG.11B
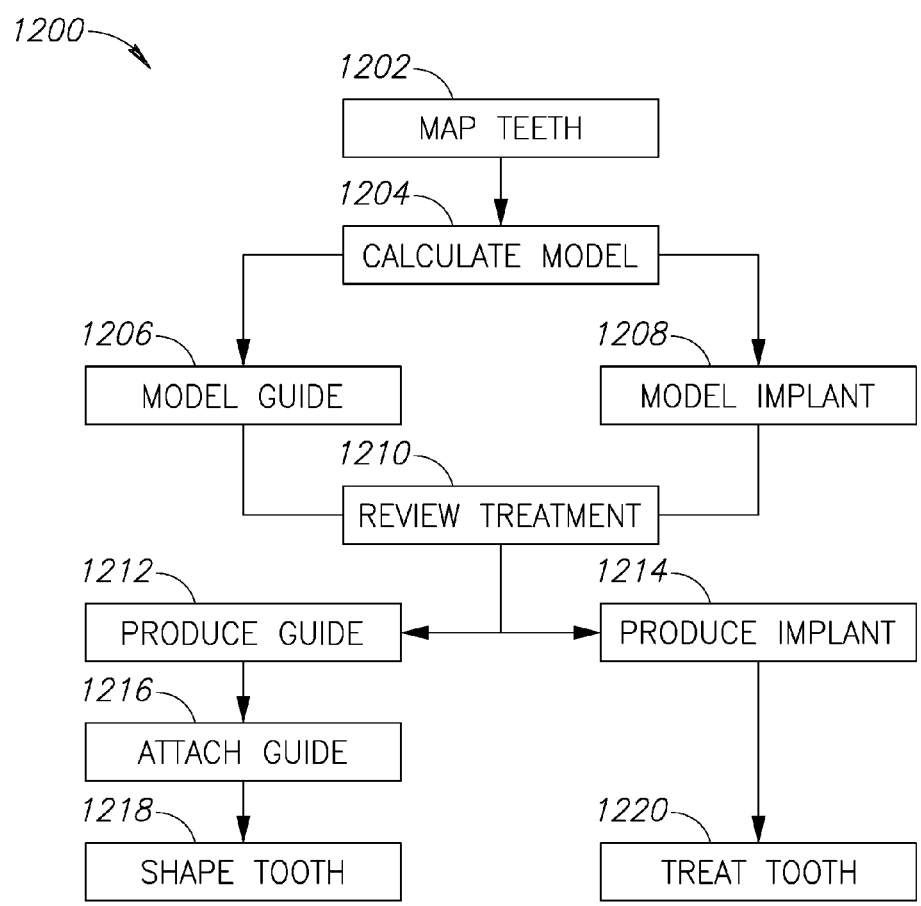
FIG.12

GUIDING ASSEMBLY FOR DENTAL RESTORATION PROCEDURES

CROSS REFERENCE TO RELATED APPLICATIONS

This application is a national phase of PCT Patent Application No. PCT/IL2016/050260 filed Mar. 9, 2016, which claims the benefit of priority of Israel Patent Application No. 237637, filed Mar. 9, 2015, and Israel Patent Application No. 242477, filed Nov. 5, 2015, all entitled "GUIDING APPARATUS FOR USE IN DENTAL RESTORATION PROCEDURES. The contents of the above applications are all incorporated by reference as if fully set forth herein in their entirety.

FIELD OF THE INVENTION

The invention relates to the field of dental guiding assemblies.

BACKGROUND

Dental procedures, such as dental crown procedures, dental cap procedures, dental implant procedures, and/or the like, may require preparing a tooth by reshaping the tooth surface. An x-ray image may be taken to check the roots of the tooth, and when a root canal is not needed the tooth is reshaped. Support material may be used to fill up the tooth surface to support the crown. Once the surface is reshaped, an impression of the reshaped tooth structure may be acquired for preparing a dental restoration. For example, the tooth impression is used to make a dental crown at a specialized laboratory, sent to the dentist a few weeks later, and attached to the reshaped tooth during a second visit.

The tools that are used for reshaping are usually dental drills with dental burs attached to the drill for reshaping the tooth. The dentist chooses one of several available dental bur shapes, and files down the treated tooth with the dental bur to prepare the surface to receive the crown. The dental surgeon carefully moves the rotating dental bur across the tooth surface to remove some of the tooth material and reshape the tooth. The reshaped tooth for receiving a crown should have enough surface to support the interior of the crown for good mechanical support.

All crowns have a minimal thickness and may need some space to fit on the treated tooth to ensure that the crown has the same size as the original healthy tooth. The minimal thickness ensures the crown has adequate mechanical strength, such as for example a thickness of one or two millimeters. For example, porcelain crowns require enough ceramic thickness to reduce translucency such as 1.5 millimeters thickness, and thus a treated tooth needs to be filed down by at least 1.5 millimeter. The tooth reshaping may further require a tapering, so that a dental crown may be easily attached to the tooth. Additionally, a margin must be taken into account when reshaping a tooth, such as a shoulder, a chamfer, a bevel, and/or the like.

Similar procedures exist for dental overlays, dental ¾ crowns, dental implants, dental prostheses, prosthetic crown, and/or the like. As used herein, the term dental restoration means any artificial material used to restore a tooth structure, such as a dental crown, an inlay, an overlay, a dental implant, and the like.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a dental guidance assembly, comprising a rigid body comprising one or more tooth-shaped recesses and a coupling structure. The dental guidance assembly comprises at least two dental bur guides. Each dental bur guide is structured to securely and removably couple to the coupling structure. Each dental bur guide comprises an elongated slot having the following measurements of a length of 4 to 40 millimeters, a width of 1 to 4 millimeters, and a depth of 2 to 10 millimeters. The elongated slot extends along a portion of a circumference of a treated tooth. The elongated slots of the at least two dental bur guides have complementary structures, such that, together, the elongated slots are configured to facilitate a limitation of the motion of a dental bur to an entirety of the circumference of a treated tooth, and a depth suitable to form a shoulder on the treated tooth, for receiving a dental restoration.

In some embodiments, the coupling structure is ridge-shaped, where the ridge surrounds a void for treating a tooth in the rigid body, and where the ridge is on a side of the rigid body opposing the side comprising the tooth-shaped recesses.

In some embodiments, the motion of the dental bur is limited by the coupling structure and a central portion of each dental bur guide.

In some embodiments, each dental bur guide is comprised of a second coupling structure configured to securely and removably couple to the coupling structure, a central structure, and a mechanical element connecting between the second coupling structure and the central structure and the elongated slot.

In some embodiments, the elongated slot is formed between the coupling structure and the central structure, wherein the coupling structure is configured as a ridge-shaped structure, wherein the ridge surrounds a void for treating a tooth in the rigid body, and wherein the ridge is on a side of the rigid body opposing the side comprising the tooth-shaped recesses.

In some embodiments, the elongated slot is formed between the second coupling structure and the central structure, wherein the second coupling structure is configured as a ridge-shaped structure, wherein the ridge surrounds a void for treating a tooth in the rigid body, and wherein the ridge is on a side of the rigid body opposing the side comprising the tooth-shaped recesses.

In some embodiments, the dental guidance assembly further comprises a liner. The liner comprises a sleeve configured to fit snuggly in the elongated slot and through which the dental bur is operated. The liner comprises an annular protruding ring surrounding one end of the sleeve that has an outer diameter larger than the elongated slot by at least 0.5 millimeters.

In some embodiments, the tooth-shaped recesses and the coupling structure are each located on different sides of the rigid body.

In some embodiments, the limitation is in a location, a height, and an angle of the dental bur.

In some embodiments, the dental guidance assembly further comprises a surface reshaping guide comprising a motion limiting structure for limiting the motion of a dental bur when performing an occlusal surface reshaping procedure.

There is provided, in accordance with an embodiment, a dental guidance assembly comprising a rigid body having one or more tooth-shaped recesses and a ridge. The dental guidance assembly comprises a dental bur anchor comprising a dental bur sleeve, an opposing mechanical element, and a connecting arm between the dental bur sleeve and the opposing mechanical element, thereby forming a ridge anchoring structure configured to snugly glide along the ridge. the ridge is structured to completely surround a treated tooth, and is of a height, shape, and position configured to limit a motion of a dental bur to form a shoulder around the complete circumference of the treated tooth for receiving a dental restoration when the dental bur is inserted into the dental bur sleeve and the dental bur anchor is glided along the ridge.

In some embodiments, the dental bur anchor is incorporated into a dental drill.

In some embodiments, the dental bur is incorporated into the dental bur anchor.

In some embodiments, the tooth-shaped recesses and the ridge are each located on opposing sides of the rigid body.

In some embodiments, the motion of the dental bur is limited in a location, a height, and an angle of the dental bur.

In some embodiments, the dental guidance assembly further comprises a surface reshaping guide comprising a motion limiting structure for limiting the motion of a dental bur when performing an occlusal surface reshaping procedure.

There is provided, in accordance with an embodiment, a computer program product for fabricating a dental guidance assembly. The computer program product comprises a non-transitory computer readable storage medium having encoded thereon computer instructions to instruct one or more computer hardware processors to perform steps. The steps comprise receiving a three-dimensional (3D) scan of teeth of a patient. The steps comprise calculating a computerized teeth model of the teeth of the patient. The steps comprise calculating a computerized assembly model of a dental guidance assembly having the structure of a rigid body comprising one or more tooth-shaped recesses and a coupling structure. The dental guidance assembly has the structure of at least two dental bur guides. Each dental bur guide is structured to securely and removably couple to the coupling structure. Each dental bur guides comprises an elongated slot having the measurements of a length of 4 to 40 millimeters, a width of 1 to 4 millimeters, and a depth of 2 to 10 millimeters. The elongated slot extends along a portion of a circumference of a treated tooth. The elongated slots of the at least two dental bur guides have complementary structures, such that, together, the elongated slots are configured to facilitate a limitation of the motion of a dental bur. The dental bur is limited to an entirety of the circumference of a treated tooth. The dental bur is limited to a depth suitable to form a shoulder on the treated tooth, for receiving a dental restoration. The recesses are based on respective teeth of the computerized teeth model. The steps comprise preparing a set of 3D fabricator instructions for fabricating the computerized assembly model. The steps comprise sending the set of 3D fabrication instructions to a 3D fabricator, thereby fabricating the dental guidance assembly.

In some embodiments, the computer instructions instruct the computer hardware processor(s) to perform the further step of receiving a user input indicating the treated tooth.

In some embodiments, the computer instructions instruct the computer hardware processor(s) to perform the further step of presenting the computerized teeth model on a user interface connected to the computer hardware processor(s).

In some embodiments, the 3D fabricator is a 3D computerized printer or a 3D computerized milling device.

In some embodiments, the coupling structure is ridge-shaped, wherein the ridge surrounds a void for treating a tooth in the rigid body, and wherein the ridge is on a side of the rigid body opposing the side comprising the tooth-shaped recesses.

In some embodiments, the motion of the dental bur is limited by the coupling structure and a central portion of each dental bur guide.

In some embodiments, each dental bur guide comprises a second coupling structure configured to securely and removably couple to the coupling structure. Each dental bur guide comprises a central structure. Each dental bur guide comprises a mechanical element connecting between the second coupling structure and the central structure. Each dental bur guide comprises an elongated slot.

In some embodiments, the elongated slot is formed between the coupling structure and the central structure, wherein the coupling structure is configured as a ridge-shaped structure, wherein the ridge surrounds a void for treating a tooth in the rigid body, and wherein the ridge is on a side of the rigid body opposing the side comprising the tooth-shaped recesses.

In some embodiments, the elongated slot is formed between the second coupling structure and the central structure, wherein the second coupling structure is configured as a ridge-shaped structure, wherein the ridge surrounds a void for treating a tooth in the rigid body, and wherein the ridge is on a side of the rigid body opposing the side comprising the tooth-shaped recesses.

In some embodiments, computer program product further comprises a liner. The liner comprises a sleeve configured to fit snuggly in the elongated slot and through which the dental bur is operated. The liner comprises an annular protruding ring surrounding one end of the sleeve that has an outer diameter larger than the elongated slot by at least 0.5 millimeters.

In some embodiments, the tooth-shaped recesses and the coupling structure are each located on different sides of the rigid body.

In some embodiments, the limitation is in a location, a height, and an angle of the dental bur.

In some embodiments, the computer program product further comprises a surface reshaping guide comprising a motion limiting structure for limiting the motion of a dental bur when performing an occlusal surface reshaping procedure.

There is provided, in accordance with an embodiment, a computerized system for fabricating a dental guidance assembly. The computerized system comprises hardware processor(s). The computerized system comprises a 3D fabricator digitally connected to the hardware processor(s). The computerized system comprises a non-transitory computer readable storage medium having encoded thereon computer instructions to instruct the computer hardware processor(s) to perform the automatic steps. The steps comprise receiving a three-dimensional (3D) scan of teeth of a patient. The steps comprise calculating a computerized teeth model of the teeth of the patient. The steps comprise calculating a computerized assembly model of a dental guidance assembly. The dental guidance assembly has the structure of a rigid body comprising one or more tooth-shaped recesses and a coupling structure. The dental guidance assembly has at least two dental bur guides that are each structured to securely and removably couple to the coupling structure. Each dental bur guide comprises an elongated slot. The elongated slot has the measurements of a length of 4 to 40 millimeters, a width of 1 to 4 millimeters, and a depth of 2 to 10 millimeters. The elongated slot extends along a portion of a circumference of a treated tooth. The elongated slots of the at least two dental bur guides have complementary structures, such that, together, the elongated slots are configured to facilitate a limitation of the motion of a dental bur. The dental bur is limited to an entirety of the circumference of a treated tooth. The dental bur is limited to a depth suitable to form a shoulder on the treated tooth, for receiving a dental restoration. The recesses are based on respective teeth of the computerized teeth model. The steps comprise preparing a set of 3D fabricator instructions for fabricating the computerized assembly model. The steps comprise sending the set of 3D fabricator instructions to the 3D fabricator, thereby fabricating the dental guidance assembly.

In some embodiments, the computer instructions instruct the computer hardware processor(s) to perform the further step of receiving a user input indicating the treated tooth.

In some embodiments, the computer instructions instruct the computer hardware processor(s) to perform the further step of presenting the computerized teeth model on a user interface connected to the computer hardware processor(s).

In some embodiments, the 3D fabricator is a 3D computerized printer or a 3D computerized milling device.

In some embodiments, the coupling structure is ridge-shaped, wherein the ridge surrounds a void for treating a tooth in the rigid body, and wherein the ridge is on a side of the rigid body opposing the side comprising the tooth-shaped recesses.

In some embodiments, the motion of the dental bur is limited by the coupling structure and a central portion of each dental bur guide.

In some embodiments, each dental bur guide comprises a second coupling structure configured to securely and removably couple to the coupling structure. Each dental bur guide comprises a central structure and a mechanical element connecting between the second coupling structure and the central structure. Each dental bur guide comprises the elongated slot.

In some embodiments, the elongated slot is formed between the coupling structure and the central structure, wherein the coupling structure is configured as a ridge-shaped structure, wherein the ridge surrounds a void for treating a tooth in the rigid body, and wherein the ridge is on a side of the rigid body opposing the side comprising the tooth-shaped recesses.

In some embodiments, the elongated slot is formed between the second coupling structure and the central structure, wherein the second coupling structure is configured as a ridge-shaped structure, wherein the ridge surrounds a void for treating a tooth in the rigid body, and wherein the ridge is on a side of the rigid body opposing the side comprising the tooth-shaped recesses.

In some embodiments, the computer program product further comprises a liner. The liner comprises a sleeve configured to fit snuggly in the elongated slot and through which the dental bur is operated. The liner comprises an annular protruding ring surrounding one end of the sleeve that has an outer diameter larger than the elongated slot by at least 0.5 millimeters.

In some embodiments, the tooth-shaped recesses and the coupling structure are each located on different sides of the rigid body.

In some embodiments, the limitation is in a location, a height, and an angle of the dental bur.

In some embodiments, the computer program product further comprises a surface reshaping guide comprising a motion limiting structure for limiting the motion of a dental bur when performing an occlusal surface reshaping procedure.

There is provided, in accordance with an embodiment, a computer program product for fabricating a dental guidance assembly. The computer program product comprises a non-transitory computer readable storage medium having encoded thereon computer instructions to instruct computer hardware processor(s) to perform automatic steps. The steps comprise receiving a three-dimensional (3D) scan of teeth of a patient. The steps comprise calculating a computerized teeth model of the teeth of the patient. The steps comprise calculating a computerized assembly model of a dental guidance assembly having the structure of a rigid body having one or more tooth-shaped recesses and a ridge. The structure has a dental bur anchor comprising a dental bur sleeve, an opposing mechanical element, and a connecting arm between the dental bur sleeve and the opposing mechanical element, thereby forming a ridge anchoring structure configured to snugly glide along the ridge. The ridge is structured to completely surround a treated tooth. The ridge is of a height, shape, and position configured to limit a motion of a dental bur to form a shoulder around the complete circumference of the treated tooth for receiving a dental restoration when the dental bur is inserted into the dental bur sleeve and the dental bur anchor is glided along the ridge. The recesses are based on respective teeth of the computerized teeth model. The steps comprise preparing a set of 3D fabricator instructions for fabricating the computerized assembly model. The steps comprise sending the set of 3D fabricator instructions to a 3D fabricator, thereby fabricating the dental guidance assembly.

In some embodiments, the computer instructions instruct the computer hardware processor(s) to perform the further step of receiving a user input indicating the treated tooth.

In some embodiments, the computer instructions instruct the computer hardware processor(s) to perform the further step of presenting the computerized teeth model on a user interface connected to the computer hardware processor(s).

In some embodiments, the 3D fabricator is a 3D computerized printer or a 3D computerized milling device.

In some embodiments, the dental bur anchor is incorporated into a dental drill.

In some embodiments, the dental bur is incorporated into the dental bur anchor.

In some embodiments, the tooth-shaped recesses and the ridge are each located on opposing sides of the rigid body.

In some embodiments, the motion of the dental bur is limited in a location, a height, and an angle of the dental bur.

In some embodiments, the computer program product further comprises a surface reshaping guide comprising a motion limiting structure for limiting the motion of a dental bur when performing an occlusal surface reshaping procedure.

There is provided, in accordance with an embodiment, a computerized system for fabricating a dental guidance assembly. The computerized system comprises hardware processor(s). The computerized system comprises a 3D fabricator digitally connected to the hardware processor(s). The computerized system comprises a non-transitory computer readable storage medium having encoded thereon computer instructions to instruct the computer hardware processor(s) to perform steps. The steps comprise receiving a three-dimensional (3D) scan of teeth of a patient. The steps comprise calculating a computerized teeth model of the teeth of the patient. The steps comprise calculating a computerized assembly model of a dental guidance assembly. The dental guidance assembly has the structure of a rigid body having one or more tooth-shaped recesses and a ridge. The dental guidance assembly has a dental bur anchor comprising a dental bur sleeve, an opposing mechanical element, and a connecting arm between the dental bur sleeve and the opposing mechanical element, thereby forming a ridge anchoring structure configured to snugly glide along the ridge. The ridge is structured to completely surround a treated tooth, and is of a height, shape, and position configured to limit a motion of a dental bur to form a shoulder around the complete circumference of the treated tooth for receiving a dental restoration when the dental bur is inserted into the dental bur sleeve and the dental bur anchor is glided along the ridge. The recesses are based on respective teeth of the computerized teeth model. The steps comprise preparing a set of 3D fabricator instructions for fabricating the computerized assembly model. The steps comprise sending the set of 3D fabricator instructions to the 3D fabricator, thereby fabricating the dental guidance assembly.

In some embodiments, the computer instructions instruct the computer hardware processor(s) to perform the further step of receiving a user input indicating the treated tooth.

In some embodiments, the computer instructions instruct the computer hardware processor(s) to perform the further step of presenting the computerized teeth model on a user interface connected to the computer hardware processor(s).

In some embodiments, the 3D fabricator is a 3D computerized printer or a 3D computerized milling device.

In some embodiments, the dental bur anchor is incorporated into a dental drill.

In some embodiments, the dental bur is incorporated into the dental bur anchor.

In some embodiments, the tooth-shaped recesses and the ridge are each located on opposing sides of the rigid body.

In some embodiments, the motion of the dental bur is limited in a location, a height, and an angle of the dental bur.

In some embodiments, the computerized system further comprises a surface reshaping guide comprising a motion limiting structure for limiting the motion of a dental bur when performing an occlusal surface reshaping procedure.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIG. 11A shows a schematic illustration of an attachment to a dental guiding assembly for occlusal tooth resurfacing;

FIG. 11B shows a schematic illustration of an exploded view of an attachment to a dental guiding assembly for occlusal tooth resurfacing; and FIG. 12 shows a flowchart of a method to treat a tooth with a dental guiding assembly.

DETAILED DESCRIPTION

Figure 1:
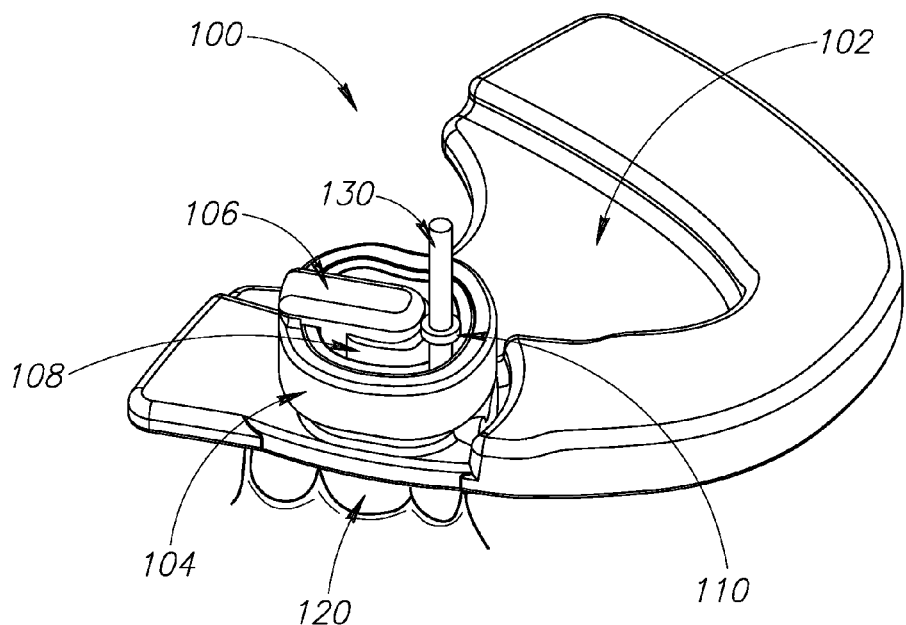
FIG. 1 shows a schematic illustration of an isometric view from the tool side of a dental guiding assembly for treating a tooth.

Disclosed herein are assemblies, computer program products, methods, and systems for use in guiding a dental tool when performing a tooth reshaping procedure. A planned three-dimensional (3D) tooth reshaping may be performed with a dedicated guide assembly comprising several parts. A rigid body part comprises one or more recesses on one side of the rigid body to mate and/or attach with one or more non-treated teeth of the subject. The rigid body comprises a gap around the treated tooth, and a coupling structure, such as a protruding ridge, near and/or surrounding the gap on the opposite side from the recesses. Another optional part may be a dental tool sleeve that provides a low friction channel for the dental bur operation. A further optional part may be an anchoring structure for limiting the motion of the sleeve, such as to allow gliding along the protruding ridge.

The planned tooth treatment may be determined by a dental surgeon, upon reviewing the status of a patient's teeth. For example, a dental surgeon receives a 3D scan of a patient's teeth, and selects one or more of the teeth for a dental restoration procedure. As embodied herein, one or more hardware processors, such as a computer with dedicated software, may automatically receive the 3D scan and the dental surgeon's selections, and automatically calculate a 3D tooth model, and a reshaping plan for the selected teeth. The dental surgeon may review the reshaping plans, and optionally modify them as needed. The hardware processor(s) may automatically selects the dental guide assembly embodiment that most efficiently performs the reshaping, such as with the least amount of time, the least amount of material, the least amount of tooth reshaping, the least expenses, and/or the like. Optionally, the dental surgeon may review hardware processor calculations and/or selections at any time, and optionally modify them as needed.

The hardware processor(s) may automatically model the parts of the assembly, and calculate the 3D fabrication instructions that will produce the assembly. The hardware processor(s) may automatically send 3D fabrication instructions to a 3D computerized fabrication device connected to the hardware processor, and once the assembly has been fabricated the dental surgeon may perform the planned tooth reshaping(s). Since the tooth reshaping is known, the dental restorations may also be fabricated similarly to and optionally at the same time as the assembly.

In one embodiment, the anchoring structure may be an annular ring protrusion around one end of the sleeve, and the coupling structure used to attach two or more dental bur guides that contain a slot to guide the sleeve along a planned location, height, and angle. In this embodiment, the sleeve protrusion limits the position of the dental bur, and each slot of the dental bur guides guide the sleeve along at least part of the circumference of the tooth. Thus the position of the dental bur may be limited as it moves around the circumference of the treated tooth and reshapes tooth surface. In this embodiment, the slots of the dental bur guides are complementary in that each slot allows covering some of the treated tooth circumference and by switching between the dental bur guides the complete circumference of the tooth may be reshaped.

Reference is now made to FIG. 1, which is a schematic illustration of an isometric view from the tool side of a dental guiding assembly 100 for treating a tooth. As used herein, the phrase "tooth side" refers to a side of a part or assembly closer to a tooth, and the phrase "tool side" refers to the side of a part or assembly closer to a dental tool. Dental guiding assembly 100 comprises a rigid body 102 which may be coupled to a dental bur guide 104 near a tooth 120 to be treated.

Rigid body 102 may be fabricated using digital 3D printing technologies, 3D computerized milling technologies, and/or the like. For example, rigid body 102 is manufactured with a desktop 3D printer in the dental surgeon's office. Rigid body may be fabricated from a biocompatible material, a plastic, a metal, a ceramic, a temporary material, a permanent material, a composite material, such as a combined resin and metal material, a reusable material, a recyclable material, a disposable material, and/or the like. For example, rigid body is fabricated from nylon (polyamide), acrylic, acrylonitrile butadiene styrene (ABS), polyetherimide, brass, alumide, carbon fiber, resin, paper, rubber, Cross-linked polyethylene (PEX, XLPE), ethylene vinyl acetate (EVA), poly(methyl methacrylate) (PMMA), polyacrylic acid (PAA), Polybutylene (PB), polybutylene terephthalate (PBT), polycarbonate (PC), polyetheretherketone (PEEK), polyester (PEs), polyethylene (PE), polyethylene terephthalate (PET, PETE), polyimide (PI), polylactic acid (PLA), polyoxymethylene (POM), polyphenyl ether (PPE), polypropylene (PP), polystyrene (PS), polysulfone (PES), polytetrafluoroethylene (PTFE), polyurethane (PU), polyvinyl chloride (PVC), polyvinylidene chloride (PVDC), styrene maleic anhydride (SMA), styrene-acrylonitrile (SAN), and/or the like.

Optionally, one part of a dental guide assembly is fabricated from one type of material and a second part from a second type of material. Optionally, a single part is partially fabricated from a first material and partially from a second material.

Dental bur guide 104 may have an elongated slot 108 which covers part of a circumference of treated tooth 120. Elongated slot 108 may be formed between a central portion 106 and rigid body 102 coupling structure. Alternatively, elongated slot 108 may be formed between a central portion 106 and dental bur guide 104 (this configuration is not shown). Assembly 100 may include a dental bur sleeve 110, through which a dental bur 130 may be operated to reshape the treated tooth 120.

Elongated slot 108 of dental bur guide 104 may have a length of 4 to 40 millimeters along the circumference of a treated tooth, a slot width of 1 to 4 millimeters, and a slot depth of 2 to 10 millimeters. As used herein, the orientations of the assembly are based on the patient orientations when the assembly is attached to a patient. The width of elongated slot 108 is the smallest dimension of elongated slot 108 on an axial plane. The length of elongated slot 108 is the length of a curve following elongated slot 108 in an axial plane. The depth of elongated slot 108 is the dimensions of elongated slot 108 in the inferior superior direction.

For example, elongated slot 108 has a length of 25 millimeters, a width of 2 millimeters, and a depth of 5 millimeters. Two such elongated slots of dental bur guides 104 of the same length may be needed to completely reshape a 40 millimeter tooth circumference, such that there are 2.5 millimeter overlaps at each end of the elongated slots between two complementary dental bur guides. Three such elongated slots of dental bur guides of the same length may be needed to completely reshape a 60 millimeter tooth circumference, such that there are 2.5 millimeter overlaps at each end of the elongated slots between two complementary dental bur guides 104. Optionally, each dental bur guide 104 and/or elongated slot 108 limits the dental bur to a different height so that any reshaping of a treated tooth is achievable.

Figure 2:
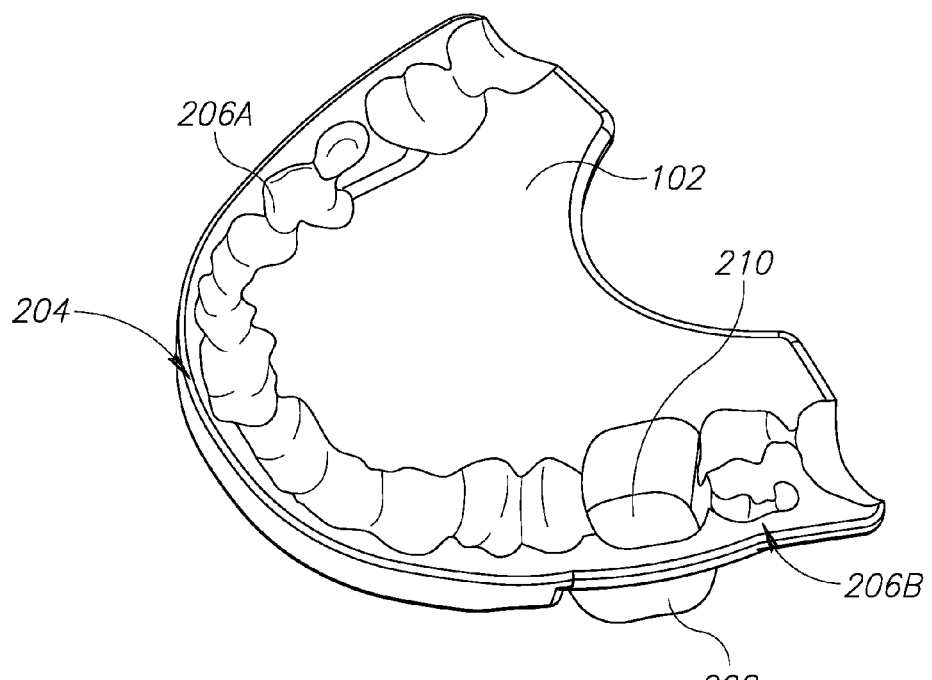
FIG. 2 shows a schematic illustration of an isometric view from the tooth side of a rigid body.

Reference is now made to FIG. 2, which is a schematic illustration of an isometric view from the tooth side of a rigid body 102. Rigid body 102 contains one or more tooth-shaped recesses 206A and 206B, such as impressions of teeth, from a 3D tooth model for a particular patient. A void 210 may be left when fabricating rigid body 102, such as a gap in rigid body 102, for dental bur access to a treated tooth. A coupling structure 208 may be located around the void 210 for attaching a dental bur guide. Edge 204 may be the anterior edge of rigid body 102, positioned towards a patient's incisor teeth during treatment.

Figure 3:
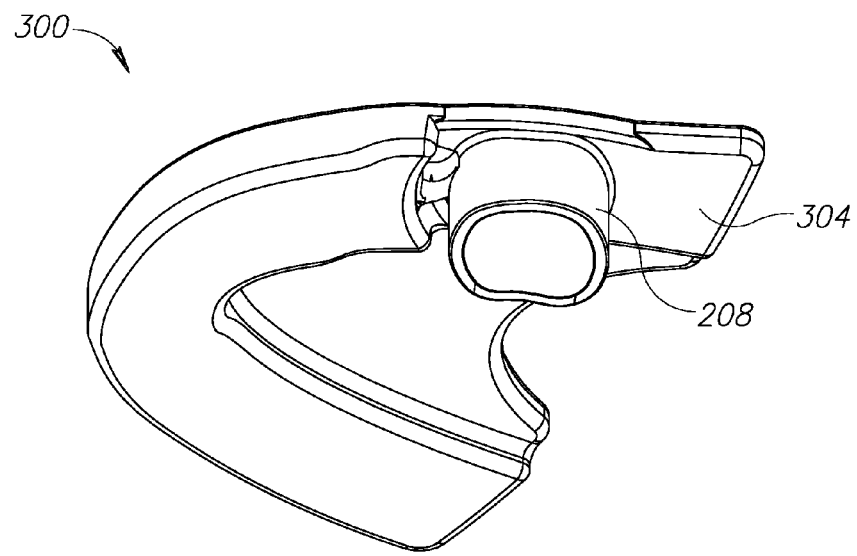
FIG. 3 shows a schematic illustration of an isometric view from the tool side of a rigid body.

Reference is now made to FIG. 3, which is a schematic illustration of an isometric view from the tool side of a rigid body 300. Rigid body 300 comprises a coupling structure 208 which may have a variable height with respect to tool side 304.

Figure 4:
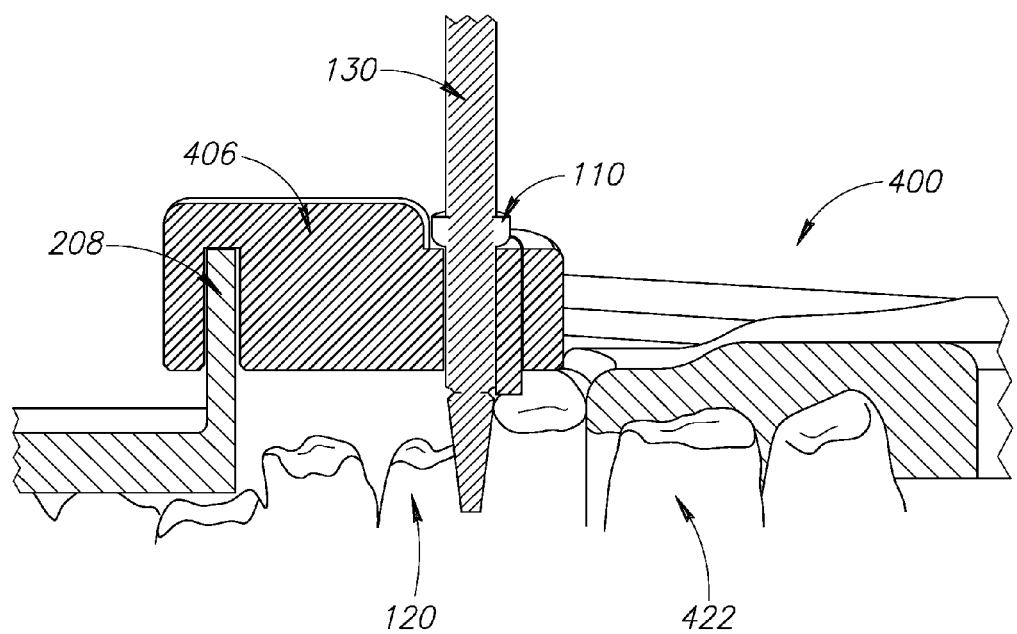
FIG. 4 shows a schematic illustration of a cross section view of a dental guiding assembly.

Reference is now made to FIG. 4, which is a schematic illustration of a cross section view of a dental guiding assembly 400. A rigid body of the assembly has recesses for attachment to a patient's teeth 422, and a void surrounding a treated tooth 420. A coupling structure 208 securely and removeably attaches a dental bur guide 406 to the rigid body. Dental bur guide 406 facilitates the generation of an elongated slot through which a sleeve 110 may be introduced for guiding a dental bur 130 around at least part of the circumference of treated tooth 120.

Figure 5:
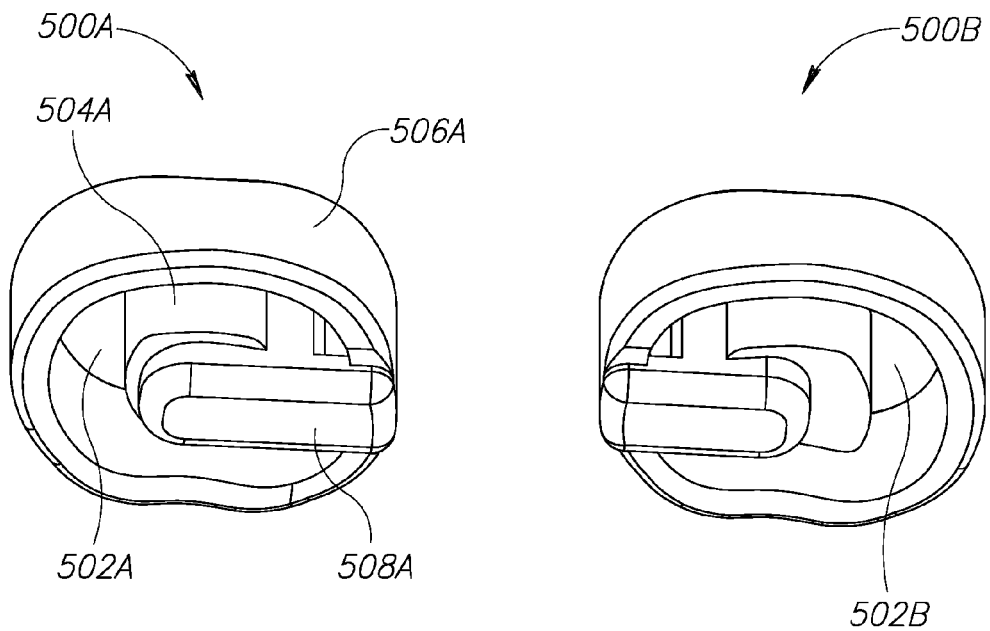
FIG. 5 shows a schematic illustration of complementary guiding parts.

Reference is now made to FIG. 5, which is a schematic illustration of complementary dental bur guides (500A and 500B). One or more complementary dental bur guides 500A and 500B may be secured by a frictional fit to coupling structure, such as 208 of FIG. 3. For example, an outer wall coupling structure 506A may have a shorter height than protruding coupling structure 208 of FIG. 3.

A retaining mechanical element 508A, which may be semi-elliptical, may extend from outer wall coupling structure 506A to an inner guiding structure 504A. An elongated slot 502A may be created between inner guiding structure 504A and protruding coupling structure 208 of FIG. 3 to limit the motion therewithin of the dental bur. Complementary dental bur guide 500B may be configured in a similar manner to dental bur guide 500A to define a complementary elongated slot 502B, such that the spatial union of the two elongated slots 502A and 502B cover the complete circumference of the treated tooth.

Figure 6:
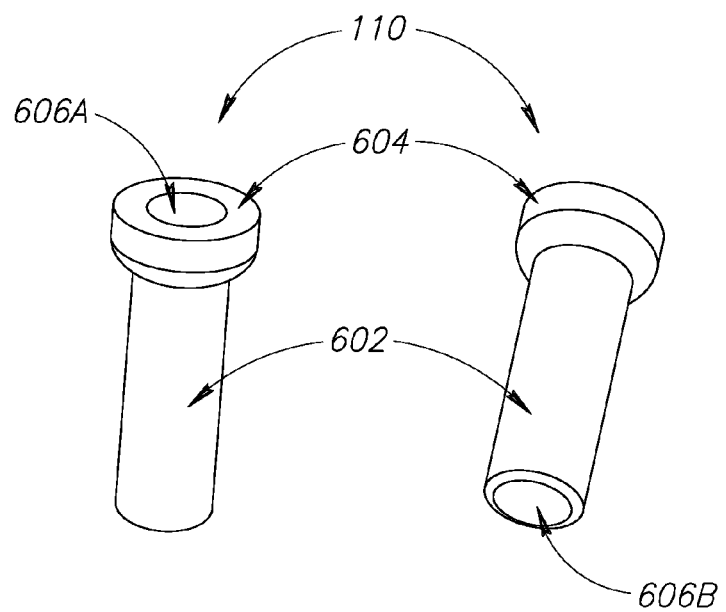
FIG. 6 shows a schematic illustration of a dental bur sleeve.

Reference is now made to FIG. 6, which is a schematic illustration of a dental bur sleeve 110. Dental bur sleeve 110 comprises a hollow sleeve portion 602, which when inserted into an elongated slot, may be configured to guide a dental bur around at least part of the circumference of a treated tooth. An annular retaining ring 604 at one end of the sleeve 110 prevents the sleeve 110 from being displaced towards the treated tooth. The hollow void 606A and 606B of the sleeve 110, may be configured to accept the shaft of a dental bur, such as a round orifice within which the dental bur rotates. An outer surface of hollow sleeve portion 602 may have a round, rectangular, trapezoid, and/or the like shape to allow smooth gliding motion along an elongated slot, and may have rounded corners to facilitate the gliding.

The length of sleeve 110 may be between 3 and 20 millimeters, hollow sleeve portion 602 may have an outer diameter of between 1 and 4 millimeters and an inner diameter of between 0.5 and 2.8 millimeters. Annular retaining ring 604 may have an outer diameter of between 1.5 and 6 millimeters and be between 0.5 to 2 millimeters in length along the axis of sleeve 110. For example, length of sleeve 110 may be 7 millimeters, hollow sleeve portion 602 may have an outer diameter of 2 millimeters, hollow sleeve portion 602 may have an inner diameter of 1.6 millimeters, annular retaining ring 604 may have an outer diameter of 3 millimeters, and annular retaining ring 604 may be 1.2 millimeters in length with a radius of curvature of 0.5 millimeters.

At times, during the course of a reshaping operation, the treated tooth may have a decayed portion which may be removed in order to ensure that the tooth structure supports the dental restoration to be connected thereto and to prevent spreading of infection. The assembly may be removed to allow access to the treated tooth for the removal of the decayed portion. Following removal of the decayed portion, restorative material such as amalgam and/or resin may be added. The assembly may be reattached to the subject, and a dental bur may be again activated along the guide(s) so that a reshaping operation may remove remnants of the restorative material or any other undesirable material. After completion, the configuration of the treated tooth reshaped structure may conform to the planned reshaped tooth structure. Optionally, a first guide may be used to remove a decayed portion of the tooth, a filling material used to build up the tooth, and a second, different guide used to reshape the tooth and filling material to the desired shape.

The dental guide assemblies described herein solve problems of repeatable and accurately guiding a dental tool, such as a dental bur, along a path for reshaping a treated tooth by the dental professional. A change in angular disposition of the dental tool may be exacerbated when the dental professional may be fatigued or stressed, leading to incompatibility between the reshaped tooth structure and the dental restoration and necessitating a modified dental restoration to be formed, thus increasing treatment time, user effort, patient discomfort, treatment cost, and/or the like.

The benefits of using a guiding assembly in dental restoration procedures may be that the angular disposition of the dental tool with respect to the tooth structure is consistently maintained. For example, by selecting the appropriate dental bur and appropriate ridge orientation, the angle of the reshaped tooth taper can be controlled accurately. For example, a tapering angle of a reshaped tooth is between 0 and 12 degrees, such as 2 degrees, 3 degrees, 4 degrees, 5, degrees, 6 degrees, 8 degrees, 10 degrees, and the like. A further benefit of a guiding assembly used in dental restoration procedures may be that the depth of the dental tool within the tooth structure is controlled and/or maintained. A further benefit of a guiding assembly may be to provide a visible delimitation of the preparation and/or restoration site.

In another embodiment, the dental guide assembly may comprise a rigid body with a ridge structure, and a dental bur anchoring element for gliding along the ridge and limiting the motion of a dental bur to a planned location, height, and angle. The dental bur anchoring element may comprise a dental bur sleeve, an arm, and an anchoring mechanical element opposing the sleeve, where the arm connects between the sleeve and opposing element. In this embodiment, the sleeve, arm, and anchoring mechanical element saddle the ridge and guide the position of the dental bur as it moves around the circumference of the treated tooth and reshapes a tooth surface. For example, the sleeve, arm and anchoring mechanical element form three contact points to saddle three points along a cross section of the ridge, and thus the anchoring element glides along the ridge as the dental bur reshapes the circumference of the treated tooth.

Figure 7:
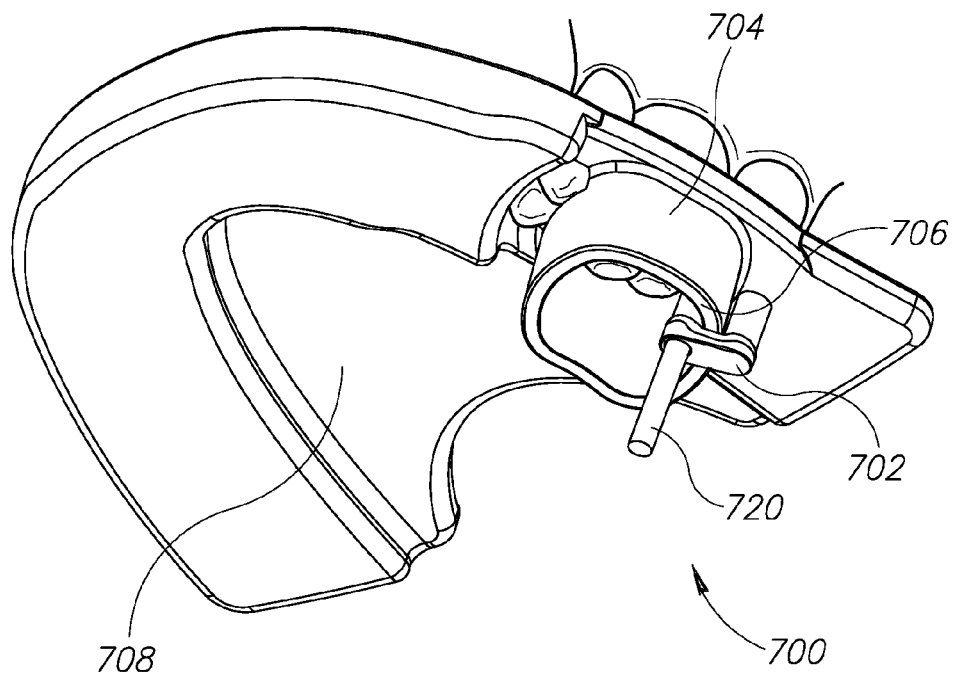
FIG. 7 shows a schematic illustration of an isometric view from the tool side of a dental guide assembly.

Reference is now made to FIG. 7, which is a schematic illustration of an isometric view from the tool side 708 of a dental guide assembly 700. Dental guide assembly 700 comprises a ridge 704 for guiding a dental bur sleeve 702 with anchoring element along a lip 706 of the ridge. Lip 706 limits the motion of a dental bur 720 as it glides along the ridge 704 around the circumference of the tooth and reaches the tooth to match a dental restoration, and/or the like. For example, a molar tooth is reshaped, but dental guide assembly 700 may be selected so as to surround any tooth needed to be reshaped.

Optionally, the coupling structure may be configured to surround only a portion of the treated tooth, for example the buccal surface of the treated tooth to which a veneer is desired to be attached. As used herein, "longitudinal" is in a direction similar to, but not identical to, the length of the dental arch between a first distal tooth to a second distal tooth. "buccal" is in a direction towards the cheeks while "lingual" is in a direction towards the tongue.

Figure 8:
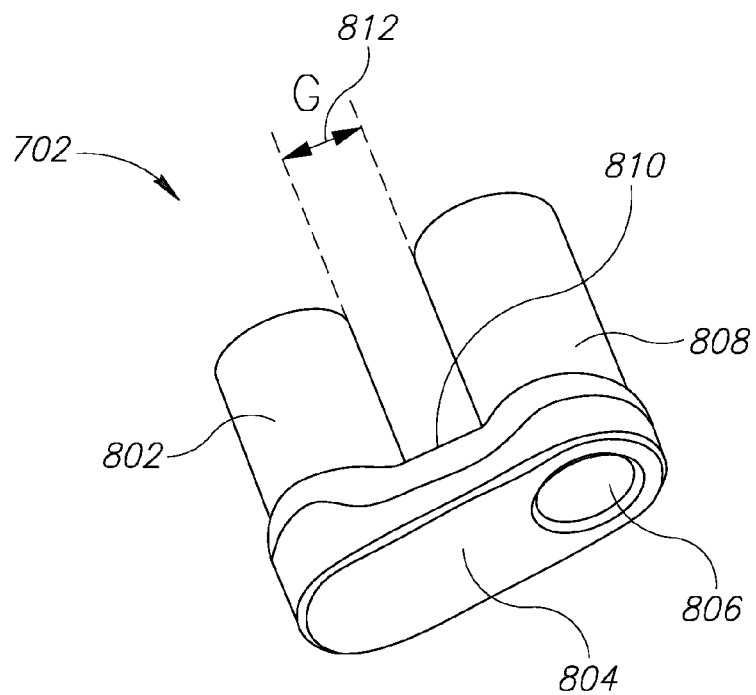
FIG. 8 shows a schematic illustration of a dental bur anchoring structure.

Reference is now made to FIG. 8, which is a schematic illustration of a dental bur anchoring structure 702. Dental bur anchoring structure 702 comprises a sleeve part 808 for holding the shaft of a dental bur, an opposing anchoring mechanical element 802 for contacting the opposing side of the ridge from sleeve 808, and an arm 804 to rigidly connect between sleeve 808 and opposing element 802. For example, the ridge may have a constant cross sectional thickness. In this example, sleeve 808 and opposing element 802 may have outer cylindrical shaped surfaces to form two parallel lines of contact at a distance G 812 between anchoring structure 702 and the ridge. The spacing G 812 may be substantially equal to, or slightly greater than, the ridge. The third point of contact may be a side 810 of arm 804 closest to the ridge.

Alternatively, the two lines of contact are not parallel or near parallel to allow easy attachment of anchoring structure 702 to the ridge. Alternatively, sleeve 808 and opposing element 802 may have a flat surface on the sides facing the ridge to allow a contact surface with the ridge instead of a contact line. Sleeve 808 and opposing element 802 length may be shorter than the height of the ridge. Sleeve 808 comprises a round aperture 806 for receiving the dental bur shaft.

Optionally, the ridge is inclined with respect to the inferior superior direction, for example defining an angle therebetween of up to 6 degrees.

Alternatively, the ridge may comprise a bead along the lip of the ridge, and a corresponding void between sleeve 808 and opposing element 802 to limit the motion of the dental bur. In this alternative example, the bead along the ridge may have one section of the ridge without the bead for attachment of anchoring structure 702 to the ridge. Alternatively, the angular limitation may be maintained by means of a tongue and groove arrangement, where one of the tongue or groove is on the lip of the ridge, and the other of the tongue or groove is on the ridge contacting surface of anchoring structure 702. For example, a protrusion extends along the ridge at a constant cross sectional shape and anchoring structure 702 has a matching groove to receive the protrusion. When the protrusion is introduced into the matching groove, the side edges of the groove may have a minimal clearance to the protrusion to enable longitudinal displacement of the holder, yet set the holder in a fixed angular relation with respect to the tooth structure.

Figure 9:
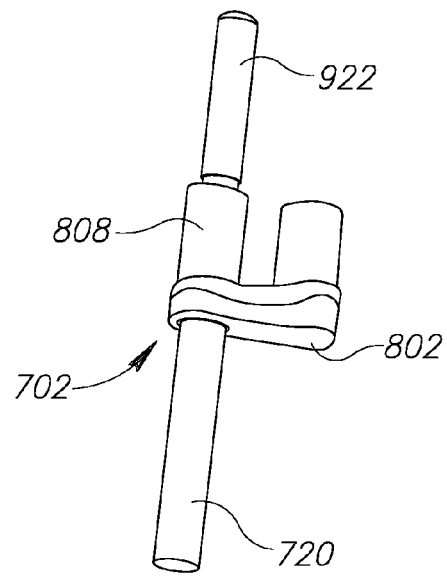
FIG. 9 shows a schematic illustration of a dental bur anchoring structure with a dental bur.

Reference is now made to FIG. 9, which is a schematic illustration of a dental bur anchoring structure 702 with a dental bur 720 and 922. This illustration shows the relation of the sleeve 808, arm 802 and the dental bur 922.

Figure 10:
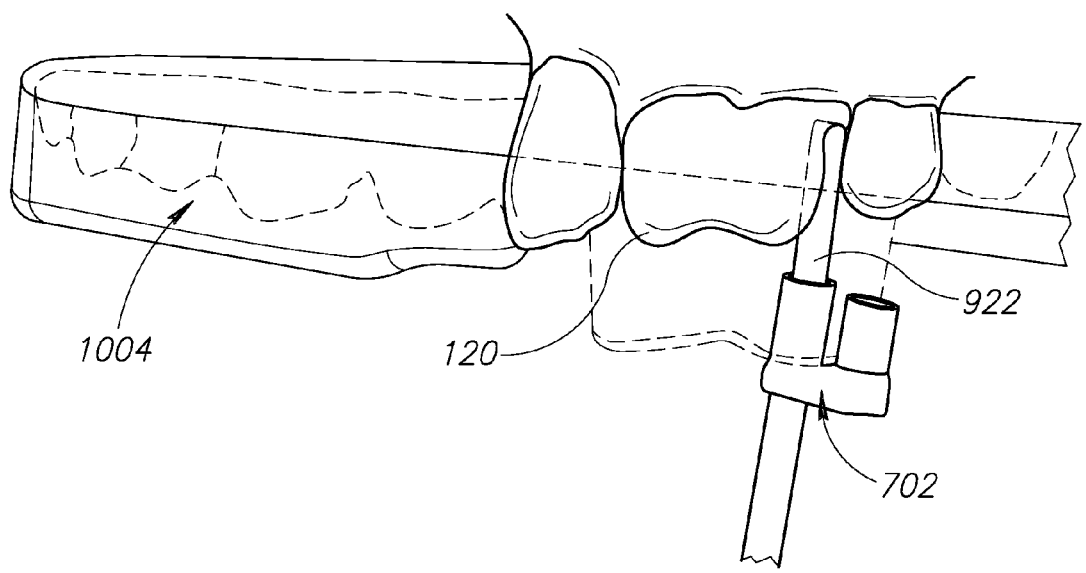
FIG. 10 shows a schematic illustration of a second dental guiding assembly during a tooth treatment.

Reference is now made to FIG. 10, which is a schematic illustration of a second dental guiding assembly during a tooth treatment. The assembly comprises a rigid body 922 with one or more tooth shaped recesses for attaching to one or more non-treated teeth 120. As an anchoring structure 702 glides along a ridge surrounding a treated tooth, a dental bur 922 reshapes the surface of a tooth for receiving a dental restoration.

In operation, the rigid body may be removeably attached to one or more teeth. The anchoring element may be attached with the dental bur to a dental drill, and may be placed in contact with the ridge, such that the dental drill may glide along the ridge while the attached dental bur reshapes the treated tooth. A dental professional may operate the dental tool to reshape a treated tooth Optionally, dental bur guide and/or rigid body comprise one or more drill guide holes for using a dental bur to drill a hole in the treated tooth. Optionally, an anchoring structure comprises an extended sleeve to better hold the dental bur shaft.

Optionally, an occlusal bur guide is used to resurface the occlusal face of a treated tooth when inserted into a coupling structure, ridge, and/or the like, such as 208 in FIG. 2. For example, a disk shaped guide comprises a disk body, a central orifice for retaining a dental bur, and a lateral motion limiting structure on the side of the disk facing the tooth is inside the void of the rigid base around the treated tooth. The dental bur is operated on a tooth inside the void of the rigid base around the treated tooth. The lateral motion limiting structure limits the motion of the dental bur on the axial plane when the structure meets the ridge, coupling structure, and/or the like. The inferior-superior motion of the dental bur is limited by the disk meeting the ridge, and thus the reshaping of the tooth on the occlusal surface is limited to the structure of the occlusal bur guide and the ridge, coupling structure, and/or the like.

Optionally, an occlusal base is used with the occlusal bur guide to allow the occlusal resurfacing of a tooth. For example, an occlusal base is attached to the coupling structure, ridge, and/or the like, to limit the motion of an occlusal bur guide when the coupling structure, ridge, and/or the like are not configured for this. For example, two dental bur guides and a sleeve are used to reshape the margins of the tooth, and an occlusal base and occlusal bur guide are used to reshape the occlusal surface of the tooth. This allows producing a single rigid base for even complex reshaping procedures, by producing smaller fitted guides that couple with the rigid base.

For example, a single rigid base comprising ridge structure and a sleeve may be used for the circumferential reshaping of a tooth and an occlusal bur guide used for occlusal reshaping. For example, a single rigid base comprising a ridge structure and a sleeve may be used for the circumferential reshaping of a tooth and an occlusal base and bur guide used for occlusal reshaping. For example, a single rigid base comprising a ridge structure, two dental bur guides, and a sleeve may be used for the circumferential reshaping of a tooth and an occlusal base and bur guide used for occlusal reshaping.

Optionally, an occlusal guiding assembly is used to reshape an occlusal surface of a tooth. Reference is now made to FIG. 11A, which is a schematic illustration of an attachment 1100 to a dental guiding assembly for occlusal tooth resurfacing. An occlusal guiding assembly attachment 1100 may comprise an occlusal base 1106 for attachment to a coupling structure of a rigid base, a ridge structure, and/or the like. Attached to base 1106 may be an arm 1104 with a pin 1112 to allow stability of the dental bur during operation. An occlusal bur guide 1116 of attachment 1100 may comprise an arm 1114 with a slot 1110 matching pin 1112. An orifice 1102 in occlusal bur guide 1116 may receive the shaft of a dental bur 1120. During operation of a dental drill, the dental surgeon may move occlusal bur guide 1116 over base 1106, but the dental bur may be limited by slot 1110, pin 1112, other matching structures between occlusal bur guide 1116 and base 1106, and/or the like, so that the occlusal surface of a treated tooth may be reshaped and the dental bur is operated in a stable manner.

Reference is now made to FIG. 11B, which shows a schematic illustration of an exploded view of an attachment to a dental guiding assembly for occlusal tooth resurfacing. An occlusal bur guide 1116 comprises a limiting structure 1136 surrounding the central orifice for insertion of a dental bur through occlusal bur guide 1116. For example, when the dental bur is operated on a tooth, occlusal bur guide 1116 limits the inferior-superior motion of the dental bur for reshaping the occlusal surface of the tooth by meeting the ridge structure which limits the dental bur from penetrating the tooth too deeply. An occlusal base 1106 may be used to alter the limiting configuration of the ridge structure, both in the inferior-superior direction using the height of occlusal base 1106, and in the axial plane using a central orifice 1126 in occlusal base 1106 that limits the lateral motion of limiting structure 1136.

Optionally, part of the occlusal surface of the tooth is reshaped.

Optionally, elements 1110 and 1112 have alternative configurations to stabilize between elements 1116 and 1106 during operation.

Attachment 1100 may limit the height of the dental bur during operation. For example, the surface of moveable part 1116 and the matching surface of base 1106 are flat surfaces so the occlusal surface of a treated tooth is reshaped in a corresponding flat surface. Attachment 1100 may selectively limit the height of the dental bur during operation. For example, the surface of moveable part 1116 and the matching surface of base 1106 are curved surfaces so the occlusal surface of a treated tooth is reshaped in a corresponding curved surface.

Optionally, a dental guide assembly is fabricated using a process, such as a computer program product comprising processor instructions, a hardware system with processor instructions stored thereon, and/or the like. Reference is now made to FIG. 12, which is a flowchart of a method 1200 to treat a tooth with a dental guiding assembly. A hardware processor may automatically receive a three-dimensional (3D) scan of the teeth, such as 3D mapping 1202 of the teeth, and automatically calculate 1204 a teeth model from the scan. The 3D teeth model, such as a digital impression 3D model, may be used to automatically model 1206 a guide assembly and automatically model 1208 (optionally) one or more dental restorations, such as one or more prostheses, optionally with manual input from a dental surgeon, such as an indication of the one or more corresponding teeth to be treated.

For example, a 3D scan is performed by an iTero® 3D digital scanner from Align Technology, Inc. For example, a 3D scan is performed by a GALILEOS® 3-D diagnostic system from Sirona Dental Systems GmbH.

Optionally, the dental surgeon reviews 1210 the treatment plan before producing the assemblies and/or dental restorations. Each assembly comprises a rigid body and optionally two or more guiding structures according to embodiments hereinabove. The rigid body comprises recesses to match one or more teeth of the 3D teeth model for attaching the rigid body to a patient. To automatically produce 1212 the guide assembly, printing and/or fabricating instructions are automatically generated for a 3D printer and/or 3D fabricator to fabricate the rigid body and other parts needed, and the printer and/or fabricator instructions are sent to a 3D printer and/or 3D fabricator attached to the hardware processor. As used herein, the phrase 3D printer means a computerized printer that receives 3D printing instructions from a hardware processor and produces a fabricated 3D object from a suitable material. For example, a ZRapid® SLA200 Rapid 3D Printer is used to fabricate a dental guide assembly. For example, a ZRapid® SLS400 Rapid 3D Printer is used to fabricate a dental guide assembly. For example, a ZRapid® SLM150 Metal 3D Printer is used to fabricate a dental guide assembly. For example, a Stratasys® Mojo® is used to fabricate a dental guide assembly. As used herein the term fabricating and/or fabricator is used to mean a computerized methods and/or device for constructing a 3D model, assembly, part, structure, and/or the like.

Optionally, the dental restoration(s) are automatically produced 1214 by the same or similar 3D fabricator using a suitable dental restoration material. Optionally, the dental restoration(s) are automatically produced 1214 by sending the corresponding 3D fabricator instructions to a manufacturing sub-contractor. Optionally, the one or more guide assemblies are automatically produced 1212 by sending the corresponding 3D fabricator instructions to the same or a different a manufacturing sub-contractor. Optionally, the dental restoration is modelled to match the occlusal surface of the corresponding teeth according to the 3D model.

During the treatment procedure, the rigid body may be attached 1216 to the non-treated teeth to serve as a basis for a coupling structure being variably shaped in accordance with a preplanned tooth structure reshaping plan. A dental tool, such as a bur, drill bit, or the like, may be guided through the sleeve as the sleeve glides along the guide to shape 1218 a treated tooth using the assembly. Once the treated tooth is reshaped, a tooth may be treated 1220, such as by attaching a dental restoration, a dental prosthesis, a tooth surface, a tooth crown, and/or the like.

Optionally, the length of a dental bur shaft and sleeve are selected to match the dental guide assembly. For example, a longer dental bur shaft may be needed to reshape the tooth using a dental guide assembly.

Optionally, a dental prosthesis is also fabricated based on a 3D teeth model. For example, a crown is fabricated to match the tooth reshaping performed using the dental guiding assembly and a contralateral tooth, an opposing tooth, a standard 3D tooth model, and/or the like. For example, Sirona Cerec dental crown manufacturing machine is used to make a dental crown. For example, IOS Technologies Inc. $Ts_{150}$ dental crown milling subsystem is used to make a dental crown.

A 3D mapping 1202 of a patient's teeth may be performed based on visible surfaces of a selected set of teeth including the treated tooth structure, for example by a digital camera or a blue laser inserted within the oral cavity. The captured images are automatically processed to calculate 1204 a 3D teeth model. Optionally, X-ray images of the same selected set of teeth may be obtained and processed to produce 3D X-ray data that is representative of both visible surfaces and gum obscured surfaces of the treated tooth. The digital impression 3D model may be processed to identify treatable regions of the treated tooth, for example in outline form. The 3D X-ray data may also be processed, if needed, to assist in calculating 1204 a 3D tooth model and/or identifying the treatable regions. Optionally, 3D tooth models may be calculated 1204 from computed tomography images, ultrasound images, panoramic teeth images, dental x-ray images, and/or the like.

A virtual reshaped tooth structure, which may be representative of the configuration of the treated tooth following the reshaping operation, may be generated when taking into account the identified treatable regions and the capabilities of the selected dental bur. A virtual prosthetic dental restoration, which may be representative of an actual dental restoration, may be configured to match a reshaped tooth surface.

The 3D tooth model may be compared with the virtual reshaped tooth structure, and the peripheral wall of the guide surrounding the treated tooth may be virtually generated to limit the operation of a dental bur. Thus the dental professional, when the dental bur is guided by the assembly, may be limited in manipulating the dental tool while it reshapes the treated tooth according to the treatment plan, such as to achieve the virtual reshaped tooth structure.

A digital model of a rigid body may be generated by using the digital impression 3D model to generate an accurate representation of tooth receiving recesses matching one or more teeth, a void area to access the treated tooth, and a coupling structure surrounding the void area. If necessary, the rigid body may be generated with two or more coupling structures for treating two or more respective teeth.

The virtually generated rigid body may be rendered and displayed for review by a dental professional, and optionally analyzed structurally to check the structural integrity of the reshaped tooth and/or the dental restoration. When the virtually generated rigid body needs to be modified manually, the dental professional may interface with an input device to input modifying data to a computerized device. After the virtually generated rigid body is approved by the dental professional, the rigid body may be produced by a computerized machining unit for selectively removing material from a block of dentally compatible material, such as polymeric material, in accordance with the virtually generated rigid body.

When an assembly comprises two or more dental bur guides, the treated tooth may be reshaped partially by each dental bur guide, and the dental bur guides used one by one till the complete tooth is reshaped according to the treatment plan.

When the dental professional desires to operate the dental tool continuously, a ridge like structure may be used to surround the tooth to guide an anchoring structure for reshaping the tooth.

The dental bur may be replaced with one having longer abrading surfaces, head, neck, shank, and/or the like. For example, when desired to connect a veneer to the anterior surface of a treated tooth. The dental bur may be replaced with one having a longer shaft, shank, and/or the like. The guiding ridge and/or slot may have different angular dispositions, to vary the reshaped surface as needed.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

What is claimed is:

1. A dental guidance assembly, comprising:
   a rigid body comprising at least one tooth-shaped recess and a coupling structure; and
   at least two dental bur guides that are each:
      structured to securely and removably couple to said coupling structure, and
      comprising an elongated slot having the following measurements:
         a length of 4 to 40 millimeters,
         a width of 1 to 4 millimeters, and
         a depth of 2 to 10 millimeters,
      wherein the elongated slot extends along a portion of a circumference of a treated tooth,
      wherein the elongated slots of said at least two dental bur guides have complementary structures, such that, together, the elongated slots are configured to facilitate a limitation of the motion of a dental bur to:
         an entirety of the circumference of a treated tooth, and
         a depth to form a shoulder on the treated tooth, for receiving a dental restoration,
      wherein said coupling structure is ridge-shaped, wherein the ridge surrounds a void for treating a tooth in the rigid body, and wherein the ridge is on a side of the rigid body opposing the side comprising the tooth-shaped recesses,
   wherein said coupling structure is ridge-shaped, wherein the ridge surrounds a void for treating a tooth in the rigid body, and wherein the ridge is on a side of the rigid body opposing the side comprising the tooth-shaped recesses.

2. The dental guidance assembly of claim 1, wherein the motion of the dental bur is limited by the coupling structure and a central portion of each dental bur guide.

3. The dental guidance assembly of claim 1, wherein each dental bur guide is comprised of:
   a second coupling structure configured to securely and removably couple to said coupling structure;
   a central structure;
   and a mechanical element connecting between the second coupling structure and the central structure; and
   the elongated slot.

4. The dental guidance assembly of claim 3, wherein the elongated slot is formed between the coupling structure and the central structure.

5. The dental guidance assembly of claim 3, wherein the elongated slot is formed between the second coupling structure and the central structure, wherein the second coupling structure is configured as a ridge-shaped structure, wherein the ridge of the second coupling structure surrounds the void for treating the tooth in the rigid body, and wherein the ridge of the second coupling structure is on a side of the rigid body opposing the side comprising the tooth-shaped recesses.

6. The dental guidance assembly of claim 1, further comprising a liner, the liner comprising:
   a sleeve configured to fit snuggly in the elongated slot and through which the dental bur is operated; and
   an annular protruding ring surrounding one end of the sleeve that has an outer diameter larger than the elongated slot by at least 0.5 millimeters.

7. The dental guidance assembly of claim 1, wherein the at least one tooth-shaped recess and the coupling structure are each located on different sides of the rigid body.

8. The dental guidance assembly of claim 1, further comprising a surface reshaping guide comprising a motion limiting strucutre for limiting the motion of a dental bur when performing an occusal surface reshaping procedure.

* * * * *